United States Patent [19]

Kaluniants et al.

[11] 4,286,065
[45] Aug. 25, 1981

[54] APPARATUS FOR CULTIVATION OF MICROORGANISMS ON GRANULAR NUTRIENT MEDIUM

[76] Inventors: Kalust A. Kaluniants, mikroraion Kapotnya, kvartal 4, 3, kv. 34.; Valentin G. Kozhemyakin, Leninsky prospekt, 85, korpus 6, kv. 45.; Irina M. Gracheva, ulitsa Panfilova, 18a, kv. 39.; Ljudmila I. Voino, ulitsa Kiprenskogo, 14, kv. 1., all of Moscow, U.S.S.R.

[21] Appl. No.: 95,667

[22] Filed: Nov. 19, 1979

[51] Int. Cl.³ .............................................. C12M 1/06
[52] U.S. Cl. .................................... 435/315; 435/304; 435/305; 435/307; 435/308; 435/309; 435/310; 435/313; 435/316; 435/813
[58] Field of Search ............... 435/304, 305, 307, 308, 435/309, 310, 313, 316, 813, 815

[56] References Cited

U.S. PATENT DOCUMENTS

| | | | |
|---|---|---|---|
| 350,472 | 10/1886 | Baldwin | 435/309 X |
| 409,956 | 8/1889 | Gent | 435/307 X |
| 3,730,846 | 5/1973 | Neubert | 435/304 |
| 3,849,255 | 11/1974 | Schlimme et al. | 435/304 |

FOREIGN PATENT DOCUMENTS 120202 1/1959 U.S.S.R. .
539939 1/1977 U.S.S.R. .

Primary Examiner—Robert J. Warden
Attorney, Agent, or Firm—Lackenbach, Lilling & Siegel

[57] ABSTRACT

The disclosed apparatus relates to the microbiological industry and can be used in the food and medical industries, as well as in agriculture for utilization of the waste and refuse of animal-breeding farms. The apparatus comprises a sealed vertically arranged vessel divided into a vertical row of sections by perforated partitions of two kinds mounted alternatingly height-wise of the vessel. Some of the partitions are made as discs arranged so that annular gaps remain between them and the vessel housing, while other partitions are in the form of flat rings; the annular gaps and the central openings of the flat rings serve as ducts for the passage of a nutrient medium into the underlying sections. Mounted above the perforated partitions are cylindrical shells serving as intermediate accumulators for the nutrient medium, and blade-type agitators adapted to urge the nutrient medium toward the annular gaps and central openings. This constructional arrangement of the apparatus provides for creating in each section appropriate conditions for intense growth of the microorganisms, and thus for enhancing the throughput of the apparatus.

5 Claims, 13 Drawing Figures

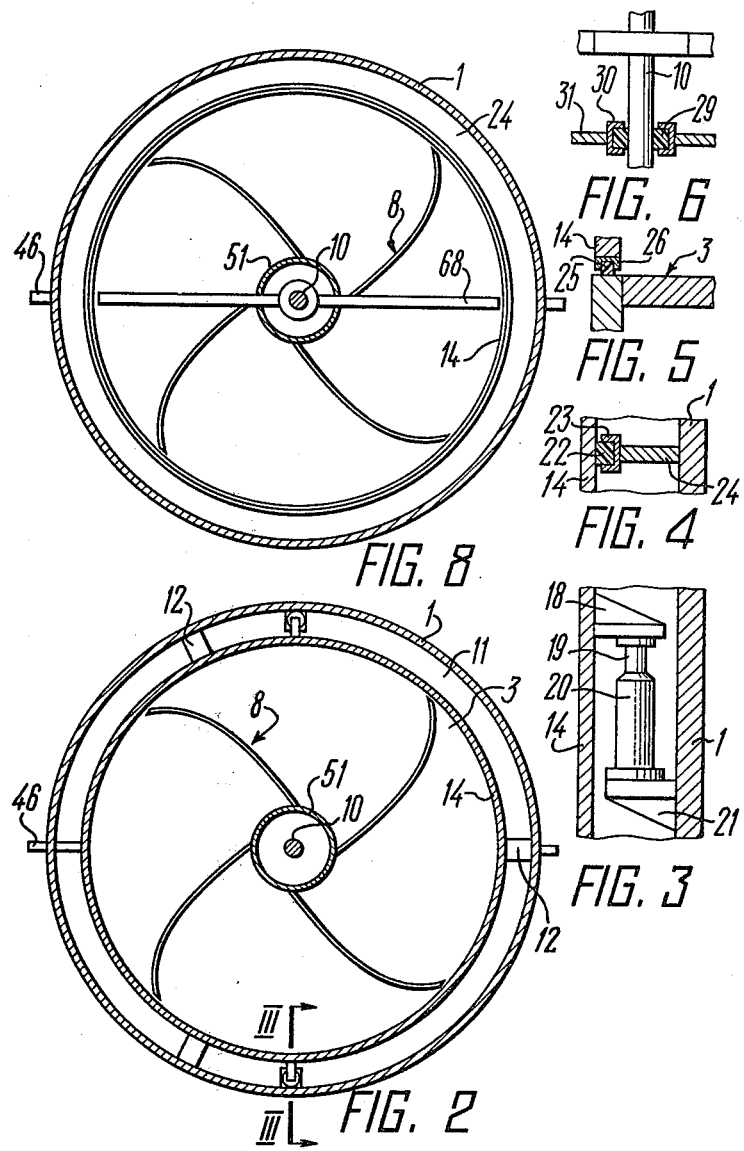

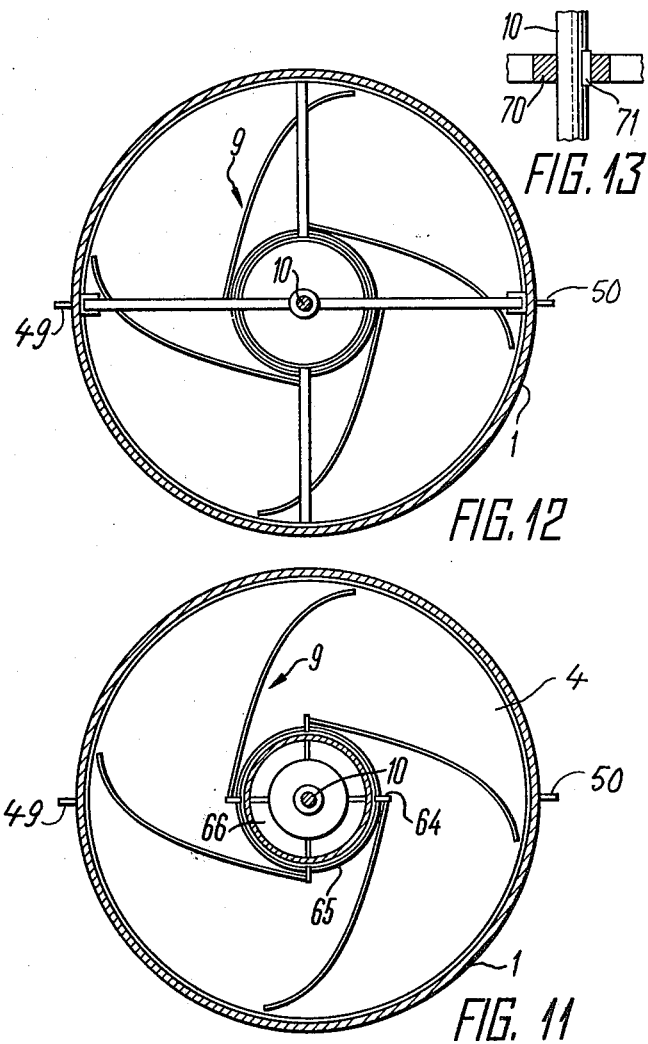

APPARATUS FOR CULTIVATION OF MICROORGANISMS ON GRANULAR NUTRIENT MEDIUM

The present invention relates to the microbiological industry, and more particularly it relates to apparatus for cultivation of microorganisms on a granular nutrient medium. The invention can be used effectively in the food and medical industries, as well as in agriculture for utilization of the waste and refuse of animal-breeding farms by biochemical technology involving growing a biological mass of either mycelia or bacteria on the solid phase of refuse, so that as a result of microbiological synthesis under aerobic conditions, the initial composition of the refuse is basically transformed into a produce suitable for practical use.

At present, various apparatus and units of different structures are used for cultivation of microorganisms, e.g. in agriculture.

However, the problem of efficient cultivation of microorganisms on agricultural refuse and waste is far from having been solved. The organic components of the solid phase include substances that are hard to oxidize, their moisture content is excessive, and their composition broadly varies depending on the actual ration of the animals. Depending on the size of a farm, the amount of refuse may be intermittent and non-uniform. Therefore, the structure of the apparatus is expected the meet strict requirements concerning the duty of conveying, loosening and aeration of the matter, as well as the cultivation duty per se.

There is known an apparatus for cultivation of microorganisms on a granula nutrient medium (see, for example, the SU Inventor's Certificates Nos. 120,202 and 539,939) comprising a vertically arranged vessel divided height-wise into sections by perforated partitions, a loading port and a discharge port, blade-type agitators in each section, mounted on a driven shaft, and pipe connections for input and output of a gas flow. Each perforated partition of the apparatus disclosed in the SU Inventor's Certificate No. 120,202 is sealingly secured to the housing and has a segment-shaped opening, the openings being angularly displaced relative to one another height-wise of the vessel and thus arranged along a helical line, which provides for the motion of the granular nutrient medium from one section into the successive one under the action of the blade-type agitators. However, the motion of the medium under the continuous action thereupon of the blades of the agitators from one section into another one has been found to suppress the development of microorganisms. This drawback becomes even more pronounced on account of the fact that in the course of being agitated, the medium is driven through a path roughly equalling the mean circumferential length of the perforated partition, which results in active stirring of the medium. Moreover, the simultaneous rotation of all the agitators and the uniform size of the segment-shaped openings impede the operation of the apparatus at the maximum throughput rating and afford, in addition to the perforations, an extra passageway for the air, which involves redistribution of the air flow within each section and affects the efficiency of aeration.

It is an object of the present invention to provide for intensification of the process of cultivation of microorganisms within each section of the apparatus and to enhance the throughput of the latter.

With this and other objects there is provided view, in an apparatus for cultivation of microorganisms on a granular nutrient medium, comprising a sealed vertically arranged vessel divided heightwise into sections by perforated partitions, a loading port and a discharge port, blade-type agitators in each section on a drive shaft extending axially from the vessel, ad pipe connections for letting a flow of gas in an out. In accordance with the invention, the vessel is divided into sections by partitions of two kinds alternating height-wise of the vessel, the first kind including partitions in the form of discs mounted to define an annular gap with the housing of the vessel, and the other kind including flat rings sealingly mounted on the housing of the vessel, the annular gaps and the central openings of the flat rings serving as ducts for the passage of the nutrient medium into respective underlying sections, a cylindrical shell being mounted above each said partition to serve as an intermediate accumulator within each respective section, the blades of the agitators overlying the respective discs having a positive angle of curvature, to advance the medium from the respective intermediate accumulator toward the annular gap and the blades of the agitators overlying the respective rings having a negative angle of curvature, to advance the medium from the respective intermediate accumulator toward the central opening of the underlying flat ring.

The proposed constructional arrangement of the partitions and of the blades of the agitators minimizes the mechanical action exerted upon the product as it advances from one section into another, which eliminates excessive stirring of the product and enhances the growth of microorganisms.

The cylindrical shells overlying each partition provide for accumulating the product in each section and thus enhance the conditions for the growth of microorganisms.

In accordance with the invention, the cylindrical shells are mounted for vertical motion to define a passage between the respective partition and the end face of the shell, as the medium is being advanced toward the ducts, which provides for creating an apparatus offering a variety of performance modes, viz. intermittent, cyclical and continuous. Furthermore, this provides for a flow passage of the required size, as the product overflows from the intermediate accumulator, in accordance with the rate of the growth of microorganisms.

In accordance with another feature of the present invention, each disc and each flat ring is made up of a set of three parallel plates, the top and bottom plates being perforated, and the central plate being solid, the plates being spaced from one another to define chambers communicating with gas flow inlet and outlet connections, which provides for stable aeration of each culture layer from above and from below, owing to the air flow being supplied through the bottom and top perforated plates.

It is expedient that the blade-type agitators overlying the discs and flat rings be connected to the drive shaft through individually controlled disengageable coupling means, to set up either periodic or cyclic cultivation duties in each section.

Auxiliary blades are preferably mounted on the drive shaft at the levels of the respective top end faces of the shells, to distribute the nutrient medium in the respective intermediate accumulators.

It is expedient that the cylindrical shells be associated with sealing means to seal off the intermediate accumulators, to stabilize the process of aeration at continuous cultivation of microorganisms, and also at intermittent and cyclical performance of the apparatus.

The disclosed apparatus utilizes the solid phase of the waste and refuse of animal-breeding farms by microbiological cultivation under aerobic conditions. It is expedient to operate the apparatus as a component of the production equipment of an animal-breeding farm, for comprehensive utilization of every product of agriculture. The employment of the disclosed apparatus for utilizing waste and refuse enables the increase of the livestock population, and enhances the environmental control. It should be pointed out that the cultivation and microbiological treatment yields a product that has nutritive properties enabling its use either as a livestock feed additive, or as a highly effective fertilizer.

The invention will be further described in connection with an embodiment of the apparatus for cultivation of microorganisms on a granular nutrient medium, constructed in accordance with the invention, with reference being made to the accompanying drawings, wherein:

FIG. 2 is a sectional view taken on line II—II of FIG. 1;

FIG. 3 is a sectional view taken on line III—III of FIG. 2;

FIG. 4 is an enlarged view of the area A of FIG. 1;

FIG. 5 is an enlarged view in a symmetrical representation of the area B of FIG. 1;

FIG. 6 is an enlarged view of the area C of FIG. 1;

FIG. 1 illustrates in more detail the sealing of the disc of the blade-type agitator relative to the shell and the flat ring, in an enlarged longitudinal sectional view;

FIG. 8 is a sectional view taken on line VIII—VIII of FIG. 1;

FIG. 11 is a sectional view taken on line XI—XI of FIG. 1;

FIG. 12 is a sectional view taken on line XII—XII of FIG. 1;

FIG. 13 is a partly longitudinal sectional view of the assembly securing the sleeve supporting the auxiliary blades.

Figure 1:
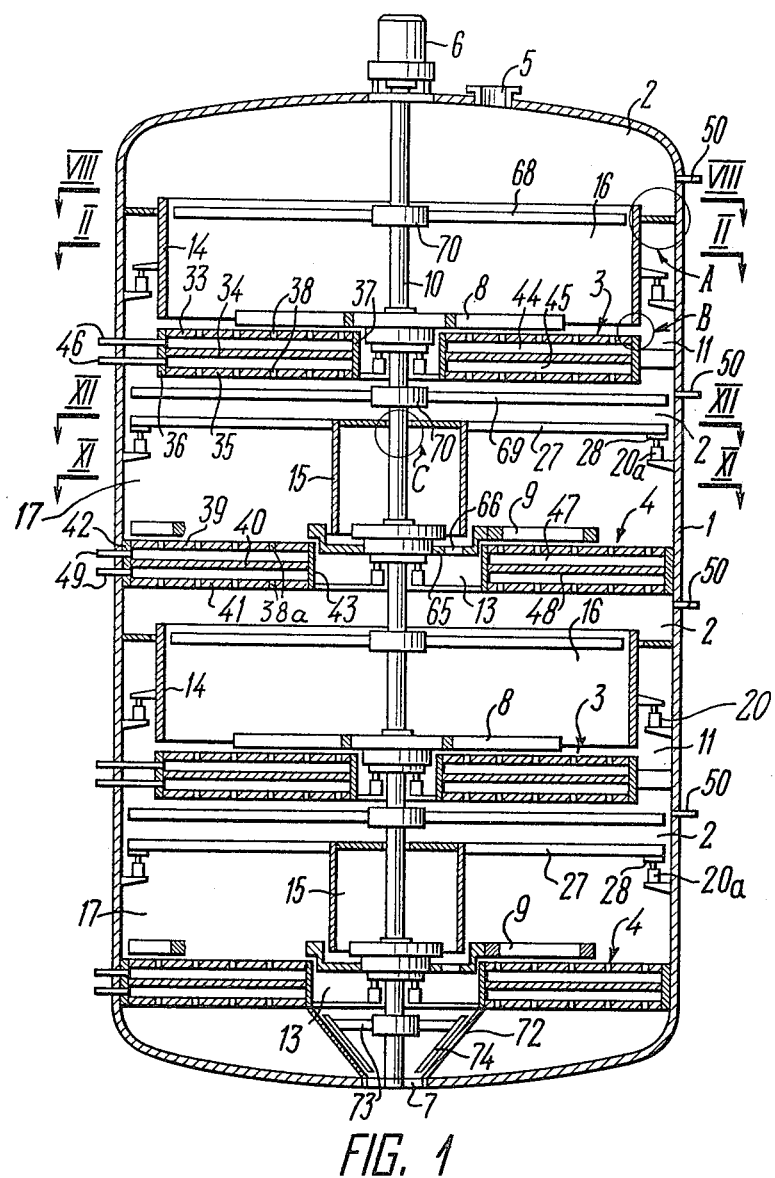
FIG. 1 is a longitudinal sectional view of an apparatus for cultivation of microorganism.

In the drawings, the apparatus for cultivation of microorganisms on a granular nutrient medium, e.g. on the waste and refuse of animal-breeding farms, comprises a sealed or fluid-tight vessel 1 (FIG. 2) arranged vertically and divided height-wise into sections 2 by alternating perforated partitions of two kinds, the first kind including discs 3 and the other kind including flat rings 4.

The upper portion of the vessel 1 defines a loading port 5 and supports a drive 6, while the lower portion or bottom of the vessel 1 defines a discharge port 7.

Overlying the discs 3 and flat rings 4 within the respective sections 2 are blade-type agitators 8 and 9 mounted on a drive shaft 10 extending axially of the vessel 1 and rotatable by the drive 6.

The discs 3 (FIG. 2) are mounted to define an annular gap 11 (FIG. 2) with the housing of the vessel 1, for which purpose they are mounted on supports 12 which in the presently described embodiments are beams of an annular cross-section, the gap 11 serving as a duct for the passage of the cultivation mass into the underlying section.

The flat rings 4 (FIG. 1) are sealingly secured to the housing of the vessel 1 in any suitable known manner, their central openings 13 defining a duct for the passage of the cultivation mass into the underlying section.

A cylindrical shell 14 or 15 is mounted to overlie each disc 3 and flat ring 4, respectively.

The disc 3 and the respective shell 14 jointly define an intermediate accumulator 16 of a cylindrical shape, adapted to accommodate the product, while the flat ring 4, the respective shell 15 and the housing of the vessel 1 like-wise define an intermediate accumulator 17 of a cylindrical shape for the product.

Each shell 14 is mounted with aid of a support 18 (FIG. 3) on the movable member 19 of an actuator 20 which may be a hydraulic or pneumatic cylinder, mounted, in its turn, on a support 21 secured to the housing of the vessel 1, the shell 14 being sealed with respect to the housing of the vessel 1 with aid of a sealing ring 22 (FIG. 4) received in a holder 23 on a ring 24 secured to the housing of the vessel 1, the shell 14 further being sealed with respect to the disc 3 (FIG. 5) with aid of a sealing ring 25 received in a holder 26 secured to the bottom end face of the shell 14.

Each shell 15 (FIG. 1) is supported by the housing of the vessel 1 with aid of bars 27 carried by a plate 28 mounted on the movable member of an actuator 20a similar to the actuator 20, supported by the housing of the vessel 1.

Figure 7:
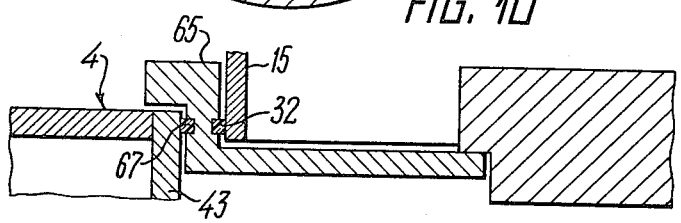

The shell 15 is sealed with respect to the drive shaft 10 with aid of a sealing ring 29 (FIG. 6) received in a holder 30 carried by a ring 31 secured to the top end face of the shell 15 (FIG. 1), the shell 15 being further sealed with respect to the flat ring 4 with aid of a sealing member 32 (FIG. 7).

With the shells 14 (FIG. 1) and 15 being mounted on the movable members of actuators, they are vertically adjustable to define a passage between the respective partition, i.e. either the disc 3 of the flat ring 4, and the adjacent end face of the shell, for advancing the product from the accumulators 16 and 17, respectively, toward the annular gap 11 and the central opening 13.

In the embodiment being described, each disc 3 is made up of a set of three parallel plates 33, 34 and 35 sealingly and concentrically arranged on support rings 36 and 37, the top and bottom plates 33 and 35, respectively, having perforates or apertures 38, whereas the central plate 34 is solid, i.e. devoid of perforations.

Each flat ring 4 is likewise made up of a set of three parallel plates 39, 40 and 41 sealing and concentrically arranged on support rings 42 and 43, the top and bottom plates 39 and 41, respectively having perforates 38a, and the central plate 40 being solid.

The plates 33, 34 and 35 are spaced from one another and define chambers 44 and 45 communicating with connection tubes 46.

The plates 39, 40 and 41 are likewise spaced from one another and define chambers 47 and 48 communicating with connection tubes 49.

The connection tubes 46 and 49 are intended for input and output of a gas flow, e.g. air flow, which is thus able to aerate the nutrient medium within the accumulators both from above and from below. Additional connection tubes 50 for in and out gas flow communicate with each section, which enhances rapid growth of microorganisms.

Figure 9:
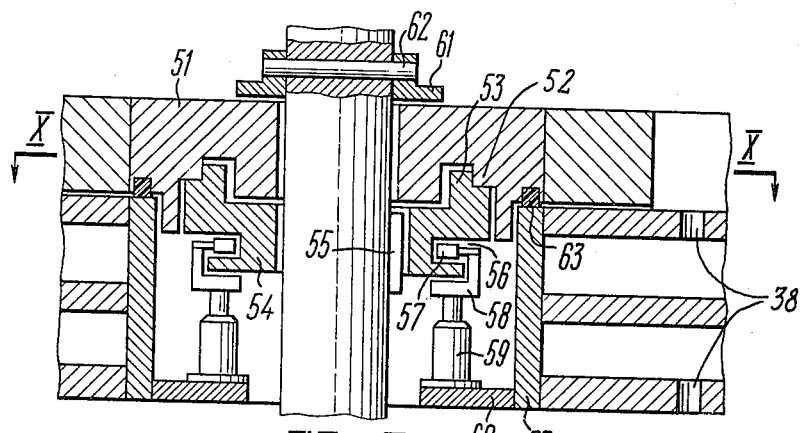
FIG. 9 is an enlarged longitudinal sectional view of the assembly securing the blades of the agitator.
Figure 10:
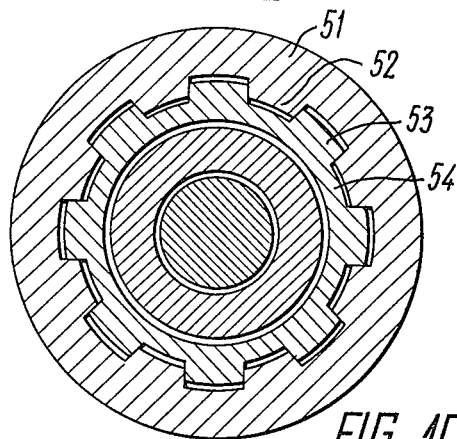
FIG. 10 is a sectional view taken on line X—X of FIG. 9.

The blade-type agitators 8 and 9 overlying, respectively, the discs 3 and the flat rings 4 are connected with the drive shaft 10 through individually controlled disengageable coupling means. Thus, the blades of the agitators 8 (FIGS. 2 and 8) are mounted on a bush or sleeve 51 connected through splines 52 (FIGS. 9 and 10) with splines 53 of a sleeve 54 movably mounted on a shaft 10 with aid of a key 55. The sleeve 54 has an undercut portion 56 receiving rollers 57. Each roller 57 is rotatably mounted on a fork 58 carried by the movable member of an actuator 59 which may be a pneumatic or hydraulic cylinder. The actuator 59 is mounted on a support 60 carried by the ring 37.

The sleeve 51 is retained against axial displacement upwardly of the shaft 10 by a ring 61 secured on the shaft 10 by a stud 62 and is associated with a sealing ring 63 interposed between the sleeve 51 and the ring 37 of the disc 3.

The blades of the agitator 9 (FIG. 11) are mounted on transverse studs 64 built into a disc 65. The latter has cutaway portions 66 to provide for downward flow of the product from the accumulator 17 into the duct, and a seal 67 (FIG. 7) interposed between the disc 65 and the ring 43.

The blades of the agitators 8 (FIG. 1) overlying the discs 3 have a positive or forwardly directed angle of their curvature, as it can be seen in FIGS. 2 and 8, to provide for advancing the nutrient medium from the respective accumulator 16 toward the annular gap 11, whereas the blades of the agitators 9 overlying the flat rings 4 have a negative or rearwardly directed angle of curvature, as it can be seen in FIGS. 11 and 12, to provide for advancing the nutrient medium from the respective accumulator 17 toward the central opening of the flat disc 4.

Mounted on the drive shaft 10 (FIG. 1) substantially at the levels of the top end faces of the cylindrical shells 14 and 15 are auxiliary blades 68 and 69, respectively, for distributing the nutrient medium within the corresponding accumulators 16 and 17. The auxiliary blades 68 or 69 are mounted on a respective sleeve 70 attached to the shaft 10 with aid of a key connection 71 (FIG. 13).

Arranged at the bottom of the vessel 1 (FIG. 1) above the discharge port 7 is a downwardly tapering hopper 72 accommodating an agitator with blades 73 carrying scrapers 74 to facilitate discharging of the product from the vessel.

The apparatus for cultivation of microorganisms on a granular nutrient medium operates, as follows.

The nutrient medium implanted with microorganisms, following sterilization and moistening within the limits of its fluidity, is poured by gravity into the loading port 5 of the vessel 1 into the uppermost section 2 accommodating the respective accumulator 16. The nutrient medium gradually fills the accumulator 16, and the drive 6 is energized for the auxiliary blades 68 to rotate and distribute the medium throughout the volume of the accumulator 16.

Following a predetermined period, the medium is forwarded from the uppermost section 2 into the underlying one, with the shell 14 raised by the movable member of the correspondingly energized actuator 20, and the blade-type agitator 8 is engaged. The engagement of the blade-type agitators 8 and 9 is effected by engaging the splines 53 (FIG. 9) with the splines 52, i.e. by energizing the actuator 20 and 20a to raise its movable member, so as to lift the roller 57 in the undercut portion 56 of the sleeve 54.

The rotating blades of the agitator 8 (FIG. 1) sweep the nutrient medium off the disc 3 into the passage now afforded between the raised shell 14 and the disc 3. In this way the nutrient medium is advanced by the rotating blades toward the annular gap 11 to flow therethrough into the underlying section 2, upon the flat ring 4, in which way the accumulator 17 is filled.

As the accumulator 17 is being filled, the rotating auxiliary blades 69 distribute the nutrient medium throughout its volume.

Following the predetermined period of residence of the nutrient medium in the last-mentioned section, the medium is forwarded into the underlying section, with the respective cylindrical shell 15 raised, and the agitator 9 engaged. The rotating blades of this agitator 9 sweep the nutrient medium off the respective flat ring 4 and advance it through the passage now formed between the raised shell 15 and the flat ring 4 toward the opening 13 of the latter, whereby the nutrient medium pours through the cut-away portions 66 onto the disc 3 of the underlying section, to fill the respective accumulator 16. While the nutrient medium is thus pouring from one section into another, the blades of the agitators 8 and 9 engage and radially displace a thin bottom layer of the entire body of the nutrient filling the closed intermediate accumulators. The nutrient medium resettles by gravity onto the respective supporting partition, and the conditions for the growth of microorganisms therein are practically unaffected.

To discharge from the apparatus the product obtained as a result of the growth of microorganisms in the nutrient medium, the discharge port 7 is opened, whereafter the product coming from the bottommost section, loosened by the blades 73 and scrapers 74, pours out of the hopper 72.

With the apparatus operated in the intermittent mode, the sections are successively filled from bottom to top of the apparatus with the implanted nutrient medium, via the overlying sections, with the shells 14 and 15 raised above the respective partitions, and the blade-type agitators 8 and 9 engaged into operation.

With all the sections thus filled, the blade-type agitators are disengaged, and the shells are lowered to define the respective individual sealed-away sections wherein cultivation is carried out through all stages of growth, without transferring the medium between the sections.

With the apparatus operated in the cyclic mode, the cylindrical shells 14 and 15 are raised above the respective partitions, while the blade-type agitators 8 and 9 are engaged solely for transferring the medium from one section into the successive one, following the completion of the corresponding stage of the growth. The described four-section embodiment of the disclosed apparatus, illustrated in FIG. 1, is preferably operated in this case so that the first or lag-phase stage of the growth is conducted in the first (from top) section, the exponential stage of the growth is conducted in the second section, the stationary growth is conducted in the third section, and the final product generation stage is conducted in the fourth section. With this pattern adopted, the nutrient medium is cyclically transferred from one section into the underlying one every one fourth of the total cultivation time.

If the cultivation is carried out in a continuous mode, the cylindrical shells 14 and 15 are raised to a height providing a rate of pouring the nutrient medium off the discs 3 and rings 4 into the annular gaps 11 and openings 13, respectively, such that a stable layer of the medium should be maintained in every section, and the required total time of residence of the medium in the apparatus should be ensured.

The provision of the required humidity and temperature characteristics of the cultivation process at each stage, and the required time of residence of the nutrient medium in each section are ensured in any suitable known manner, in accordance with the given initial composition and the adopted technology.

Aeration of the nutrient medium is effected by a flow of air through the connections 46, 49 and 50.

A prototype of the presently disclosed apparatus was operated to cultivate mycelia on the solid phase of pig manure with 60 percent moisture content. The product yielded by the process was devoid of the manure odor and contained proteins, ferments, amino-acids and vitamins.

What is claimed is:

1. An apparatus for cultivating microorganisms on a granular nutrient medium, comprising: a fluid tight vessel which houses: a vertical arrangement of perforated partitions dividing said vessel height-wise into a plurality of sections, said partitions being a first kind and a second kind alternatingly arranged height-wise of the vessel; the first kind including discs mounted to define an annular gap with the housing of said vessel, and the second kind including flat rings with a central opening, sealingly secured on the housing of said vessel, the annular gaps between the housing of said vessel and the central openings of the flat rings defining ducts for the passage of the nutrient medium into the underlying sections; cylindrical shells overlying each of said perforated partitions and defining in each respective section intermediate accumulators of the nutrient medium, wherein each said shell is mounted for vertical displacement, to define selectively a passage between said respective perforated partition and said shell for advancing the nutrient medium toward said ducts; and means for selective vertical reciprocation of said cylindrical shells; a drive shaft extending along the axis of said vessel; blade-type agitators accommodated in each said section of the drive shaft above said perforated partitions, that is, above said discs and flat rings; the blades of said agitators overlying said discs having a positive angle of curvature, to advance the nutrient medium from said intermediate accumulators toward said annular gaps; the blades of said agitators overlying said flat rings having a negative angle of curvature, to advance the nutrient medium from said intermediate accumulators toward the central opening of said flat rings; a loading port at the top of said vessel; a discharge port at the bottom of said vessel; connections for inlet and outlet gas flow communicating with said sections of said vessel.

2. An apparatus as set forth in claim 1, wherein each said disc and each said flat ring is made of a set of three parallel plates of which the top and bottom plates are perforated, and the central one is solid, said plates being spaced from one another to define chambers therebetween; the apparatus further comprising connections for inlet and outlet gas flow, communicating with said chambers.

3. An apparatus as set forth in claim 2, wherein said cylindrical shells are provided with sealing means, for sealing away said intermediate accumulators.

4. An apparatus as set forth in claim 1, wherein said blade-type agitators overlying said discs and flat rings are coupled with said drive shaft through individually controlled disengageable coupling means.

5. An apparatus as set forth in claim 4, comprising auxiliary blades mounted on said drive shaft substantially at the top levels of said cylindrical shells, adapted to distribute the nutrient medium within the respective intermediate accumulators, as the nutrient medium is pouring from the overlying section.

* * * * *